United States Patent [19]
Boegli et al.

[11] Patent Number: 4,501,145
[45] Date of Patent: Feb. 26, 1985

[54] IMMERSION THERMAL EXCHANGE PARAMETER DETERMINATION

[75] Inventors: Jean-Charles Boegli, Lucinges, France; Yves Trouilhet, Vesenaz, Switzerland

[73] Assignee: Battelle Memorial Institute, Carouge, Switzerland

[21] Appl. No.: 486,960
[22] PCT Filed: Jul. 9, 1982
[86] PCT No.: PCT/CH82/00087
 § 371 Date: Mar. 10, 1983
 § 102(e) Date: Mar. 10, 1983
[87] PCT Pub. No.: WO83/00227
 PCT Pub. Date: Jan. 20, 1983

[30] Foreign Application Priority Data
Jul. 13, 1981 [CH] Switzerland .......... 4563/81

[51] Int. Cl.³ .......... G01F 1/68; G01N 27/18
[52] U.S. Cl. .......... 73/204; 374/44
[58] Field of Search .......... 73/204; 374/44, 45, 374/43

[56] References Cited
U.S. PATENT DOCUMENTS

| | | | |
|---|---|---|---|
| 2,330,599 | 9/1943 | Kuehni | 374/44 |
| 2,730,894 | 1/1956 | Husa | 374/43 |
| 3,498,128 | 3/1970 | Calvet | 73/204 |
| 3,587,318 | 6/1971 | Belugou | 73/204 |
| 3,719,083 | 3/1973 | Morris et al. | 73/204 |
| 3,905,230 | 9/1975 | Calvet et al. | 73/204 |

Primary Examiner—Herbert Goldstein
Attorney, Agent, or Firm—Karl F. Ross; Herbert Dubno

[57] ABSTRACT

This process consists in raising the temperature of a probe immersed in the fluid to a temperature threshold corresponding to an electric resistance ($R_1$), in measuring at least a second temperature threshold corresponding to a second resistance ($R_2$, $R_3$), in measuring the time elapsed between these different thresholds and in calculating a parameter of the fluid linked to the thermal transfer between the probe and the fluid, i.e., the temperature, the velocity, the viscosity, the density, the specific heat or the thermal conductivity.

3 Claims, 5 Drawing Figures

IMMERSION THERMAL EXCHANGE PARAMETER DETERMINATION

CROSS REFERENCE TO RELATED APPLICATION

This application is a national phase application corresponding to PCT/CH 82/00087 filed July 9, 1982 and based upon Swiss application 4563/81-0 filed July 13, 1981 under the International Convention.

FIELD OF THE INVENTION

This invention relates to a process for the determination of at least one instantaneous parameter of a fluid linked to the thermal exchange of a probe immersed in that fluid as well as to a device for the application of this process.

BACKGROUND OF THE INVENTION

Flow meters are known, for example, in which an electric resistivity probe depending on temperature is heated by a Joule effect while it is immersed in a stream of that fluid. Flow variations are detected as a function of variations in the electric resistance of the probe.

The flow meter of this type is the object, in particular, of patent GB No. 1 345 324. According to this patent, the heating energy for the probe is provided by a train of identical pulses separated by intervals which are sufficiently long to guarantee that the probe will be returned to its temperature of equilibrium with the fluid at the beginning of each pulse. Flow variations are detected by the variations recorded from one pulse to the other in the rate of change of the electric resistance of the probe during a pulse. This rate of change in resistance is given by the voltage variation derived from a thermistor immersed in that fluid. The slope of the voltage variation curve or the difference between the height of the front and rear sides of each pulse is detected. The voltage at the terminals of the thermistor is applied to a voltage-frequency converter the frequency of which decreases continuously as a function of the progressive decrease in voltage. The frequency which results for the duration of the pulse is then counted and the flow rate is deduced.

From the electronic point of view, the greatest part of the processing of the signal is analog in nature which leads to a relatively complex electronic circuit and which is therefore relatively expensive. In addition, the conversion of the voltage into a variable frequency covers a range of measurement which is rather small. This remark is, by the way, also true with regard to constant power heating pulses.

There are a large number of devices or processes designed to determine an instantaneous parameter of a fluid linked to the thermal exchange between that fluid and a probe immersed in that fluid. Mention may be made, for example, of patent applications FR No. 2 168 458, DAS No. 1 252 437, CH No. 491 375 as well as U.S. Pat. No. 4,068,526. All these documents relate to devices or processes for the determination of such a parameter on the basis of the measurement of an electric quantity characteristic of a first temperature followed, after a givena time interval, by the measurement of an electric quantity characteristic of a second temperature. Whatever the electric quantity thus measured may be, for example, voltage, this analog quantity must be converted to a digital quantity so that it can be used in a calculator programmed to determine this parameter.

This digital analog conversion makes the processing circuit more complex and therefore more expensive. Now, there are a number of applications in which a system of electronic measurement could be considered, taking into account, in particular, advances in microcomputer techniques. In order for such a measurement to be carried out rationally and the processing circuit to be manufactured at a low price, in particular, for large consumption applications, it must of course be possible to introduce digital data directly into the calculator. Therefore, the solutions described in the abovementioned documents are not adapted, without any modification, to processing by a calculator and require an entire interface which makes the circuit substantially more expensive.

OBJECT OF THE INVENTION

The object of this invention is to supply a solution which will make it possible to calculate, on a purely digital base, an instantaneous parameter of a fluid linked to the thermal exchange of a thermal probe.

To this effect, this invention relates to a process for the determination of at least one instantaneous parameter of a fluid linked to the thermal exchange of a probe immersed in that fluid, characterized by the fact that the temperature of said probe immersed in that fluid is raised to a first given value, a second value, at least, of the temperature of that probe is set, the lapse of time that has passed as the first value has gone to the second value of the temperature is measured and said instantaneous parameter is calculated.

This invention also relates to a device for the application of this process characterized by the fact that said probe is an electric measurement component at least one of the parameters of which varies as a function of temperature and by the fact that it comprises means for raising the temperature of that probe to said first value, and a threshold detector with at least two levels connected, on the one hand, to that probe, and, on the other hand, to a calculator connected to an indicator member.

Taking into account the number of parameters linked to the thermal exchange, this invention offers numerous applications, in particular, in the field of measurement of instantaneous flow rates which can be used within the framework, in particular, of savings in energy.

BRIEF DESCRIPTION OF THE DRAWING

The appended drawing illustrates, schematically, and by way of example, an embodiment and variations of a device for the application of the process which is the object of this invention. In the drawing.

SPECIFIC DESCRIPTION

Figure 1:
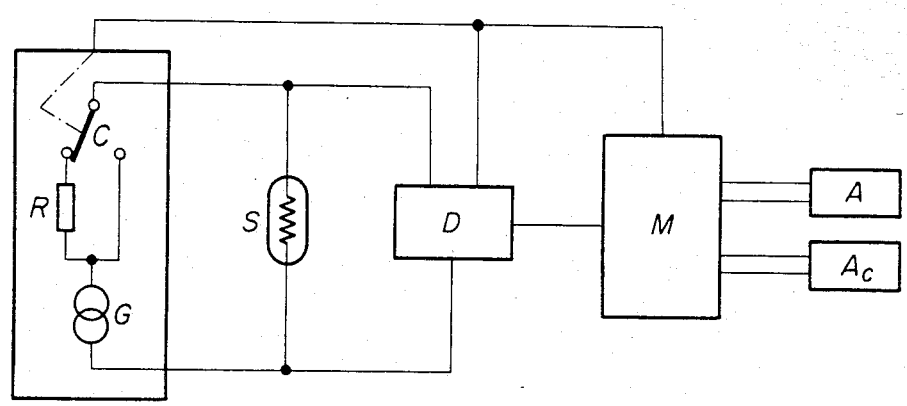
FIG. 1 is a block diagram of this device.

The process which is the object of this invention is based on the fact that when a probe is raised to a first temperature $T_0$ in a fluid, the time necessary for the temperature of that probe to reach a second or even a third temperature threshold $T_1, T_2$ is a function of all the parameters of the fluid considered which affect the thermal transfer of that probe, i.e.,: the temperature of the fluid $T_f$, its velocity v, its viscosity $\mu$, its density $\rho$, its specific heat c, its thermal conductivity $\lambda$ and its coefficient of thermal exchange.

Times $\Delta t_1$ and $\Delta t_2$ elapsed as the temperature goes from $T_0$ to $T_1$ and from $T_1$ to $T_2$ can be measured using a microprocessor after which it is possible, as will be seen subsequently, to calculate one or more of the above-mentioned parameters.

The probe used is preferably an electric resistance the resistivity of which is a function of temperature. This probe is heated periodically up to a temperature $T_0$ which is determined by measuring the voltage at the terminals of the probe, this probe being then allowed to cool down to temperature $T_1$ which corresponds to a given voltage and then to a temperature $T_2$ which corresponds to another given voltage. Using a time base incorporated into the microprocessor, times $\Delta t_1$ and $\Delta t_2$ which have elapsed between these three voltage thresholds at the probe terminals are counted. It is then possible to calculate the temperature $T_f$ of the fluid and the coefficient of thermal exchange h using the following equations:

$$(T_1 - T_f)/(T_0 - T_f) = (-hS\Delta t_1/m_s c_s)$$

$$(T_2 - T_f)/(T_1 - T_f) = (-hS\Delta t_2/m_s c_s)$$

where
$m_s$ = mass of the probe
$c_s$ = specific heat of the probe
S = probe/fluid exchange surface According to this formula, it is assumed that the probe exchanges heat only with the fluid.

The coefficient of thermal exchange h for a probe assumed to be cylindrical with a diameter d is given by the Nusselt number:

$$Nu = \frac{h\pi d}{2\lambda}$$

According to VDI Wärmeatlas:

$$Nu = 0.3 + \sqrt{Nu^2_{lam} + Nu^2_{turb}}$$

$$Nu_{lam} = 0.664 \sqrt{Re} \sqrt[3]{Pr}$$

$$Nu_{turb} = \frac{0.037 Re_e^{0.8} pr}{1 + 2.443 Re^{-0.1}(pc^{\frac{2}{3}} - 1)}$$

where $Re = \frac{v\pi dp}{2u}$ and $Pr = \frac{\mu c}{\lambda}$

It is noted that for a fluid of viscosity $\mu$, density $\rho$, specific heat c and thermal conductivity $\lambda$, all of which are known, the coefficient of thermal exchange depends on the velocity of flow v only, so that, if the fluid flow section is known, the flow rate can be deduced therefrom.

For a flowing fluid, the measurement of two time intervals makes it possible to simultaneously calculate the flow rate and the temperature.

For a fluid the velocity of which is nil, the measurement of a time interval between two temperature thresholds makes it possible to calculate the temperature when the thermal conductivity is known.

For a fluid the velocity of which is nil, the measurement of two time intervals between three temperature thresholds makes it possible to measure both the thermal conductivity of the fluid and its temperature.

In practice, a procedure is simply employed in which a probe is used the variation in resistivity of which as a function of temperature is known and the resistance at the terminals of that probe is measured in order to determine the temperature of that probe.

The measuring device shown diagrammatically in FIG. 1 comprises a probe S consisting of an electric resistance, in particular, of a thermistor the terminals of which are connected to an electric current generator G through a switch C which can connect probe S either directly to generator G, or through a resistance R the value of which is very much greater than that of probe S. The terminals of this probe are, furthermore, connected to a three level threshold detector D designed to detect three voltage thresholds corresponding to three resistance levels of the probe and in this way to three given temperatures. This threshold detector D is connected to a microprocessor M designed to calculate the desired parameters as a function of the times elapsed in order for the temperature of probe S to go from one threshold to the next. The outlet of the microprocessor is also connected to switch C so as to bring it selectively to one or the other of its positions, as well as to the threshold detector D and to a display component A. A second display component $A_c$ can be provided in order to display the total comsumption of the microprocessor by integration of the instantaneous flow rate.

Figure 2:
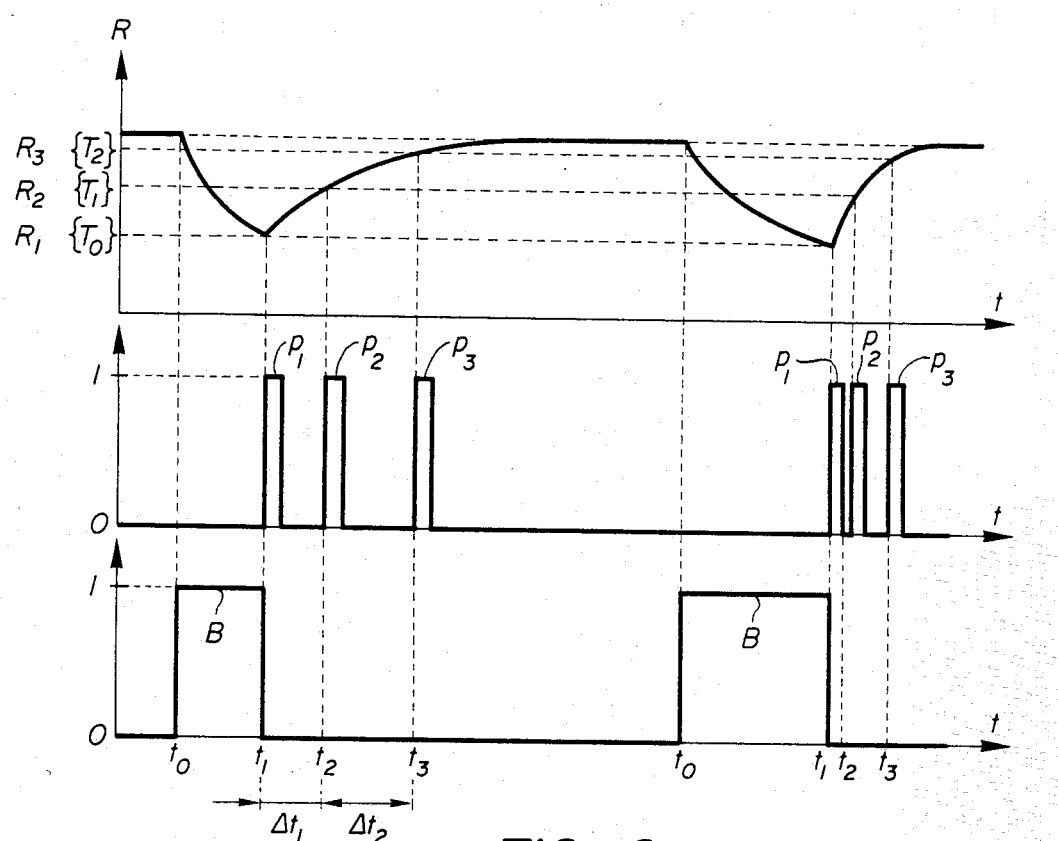
FIG. 2 is a diagram of the various signals.

In operation, at time $t_0$, a current pulse B is sent through probe S by generator G directly connected to the terminals of this probe by switch C. As soon as the electric resistance of the probe has reached a threshold value $R_1$ corresponding to a given temperature $T_o$, microprocessor M causes switch C to be tripped so as to supply probe S through resistance R chosen to provide an extremely weak measurement current, which is insufficient to heat probe S. At that moment, microprocessor M indicates to threshold detector D at which initial level the measurement curve starting at $t_1$ must be raised in order to be brought to the level $R_1$ corresponding to the end of the heating period $t_0$-$t_1$ in order for the voltage drop due to the internal resistance of the probe to be taken into account. As a varying embodiment and in order to be released from the voltage drop between the flow of heating current and that of the measurement current through probe S, consideration may be given to the division of the heating pulse B into increments, which would be interrupted by short measurement periods during which microprocessor M will cause the tripping of switch C in order to supply the probe with measurement current. In this way, the voltage measured at the probe terminals will always be comparable. Furthermore, it is possible to set the threshold $T_0$ not in coincidence with the end of the heating period but somewhere along the cooling curve. Starting at the end of pulse B, the threshold detector D which has detected the intersection of the resistance variation with the first threshold of value $R_1$ for which it has been set, sends to microprocessor M, at time $t_1$ corresponding to the end of pulse B, a pulse $P_1$ which triggers the counting operation when the resistance variation measured on the probe intersects the second threshold value corresponding to value $R_2$ and the threshold detector sends a second pulse $P_2$ to the microprocessor which counts time $\Delta t_1$ elapsed from $t_1$ to $t_2$. Finally, when the variation in resistance of probe S intersects the third threshold value $R_3$ of threshold detector D, at time $t_3$, threshold detector D sends a pulse $P_3$ to the microprocessor which counts time $\Delta t_2$ elapsed from $t_2$ to $t_3$ and calculates the parameter or parameters for which it has been programmed, according to the mathematical procedure outlined above. The resulting value is then displayed by the display component A. The same procedure is then repeated at predetermined intervals as a function of the information desired. It is not necessary to wait for the probe to return to the temperature of the fluid in order for the measurement procedure to be repeated. The latter can be started as soon as the third temperature threshold has been crossed, in the case of a measurement involving three thresholds. As an example, the diagram of FIG. 2 shows two measurement cycles, one relating to a low flow rate and the other one to a high flow rate. It can be noted that when the flow rate is low, the heating corresponding to interval $t_0$ to $t_1$ is rapid whereas the cooling from $t_1$ to $t_3$ is slow. Inversely, when the flow rate is high, the heating is slow and the cooling is rapid. As an indication, the frequency of pulses B can be of the order of several multiples of ten Hz, pulses B lasting several milliseconds. As a result, it is possible to indicate with precision and great sensitivity the instantaneous flow rate or temperature or any other parameter linked to the coefficient of thermal exchange of the probe.

The process according to the invention makes it possible, furthermore, to calculate the mass flow rate m of a fluid, which is especially valuable in the case of a gas in which density $\rho$ depends on temperature or $$m = \rho v s$$

s being the gas flow section
v being the velocity

When measuring the exchange coefficient h, v is calculated and when measuring temperature T, $\rho$ is calcualted.

A large number of applications can be considered due to the low cost of the device described. The enumeration of several of these applications has of course no restrictive character whatsoever and is simply given by way of example only.

Among these, the indication of the instantaneous consumption of an automobile vehicle can be mentioned. Such an indication can help the driver to adopt a driving mode suited to a reduced consumption by allowing him to realize at which moment his instantaneous consumption is high. It is known that at present the introduction of a microprocessor is being considered by automobile manufacturers into their entire range of products. Therefore, the instantaneous consumption indicator device represents a very small expense only which essentially comprises the three level detector and the display. By measuring the temperature and the flow rate of a fluid, consideration can be given to providing the heating installations with an instantaneous consumption indicator. The measurement of the mass flow rate can then be used to calculate the thermal energy Q, for example, in the case of a collective central heating installation in which each user is to pay his share as a function of the energy actually consumed:

$$Q = m C_p \Delta T$$

where Cp is the specific heat of the heat bearing fluid and $\Delta T$ is the difference in temperature between the input and output. Consideration is also given to a room by room management and programming of the heating in a given apartment using a microprocessor. The consumption indicator might indicate at any moment the value of this consumption, for example, in Kcal, for example room by room or for the apartment as a whole.

As seen previously, the calculation of the instantaneous parameter linked to the thermal exchange of the probe is a function of the mass of that probe. Now, depending on the nature of the fluid one parameter of which is to be calculated, substances may deposit onto the probe and change thereby its mass and, as a result, the specific heat, thus modifying the value of the parameters calculated. In such a case, it is contemplated to carry out two measurements beforehand at given temperatures but while making sure that the velocity of flow of the fluid is nil, which makes it possible to calibrate the measurement process and to thus be released from the variations in mass of the probe. In the case of an automobile vehicle, this calibration can be carried out when the driver turns the ignition key, before the actual starting of the motor, i.e., before the gasoline flows between the tank and the carburator.

Figure 3:
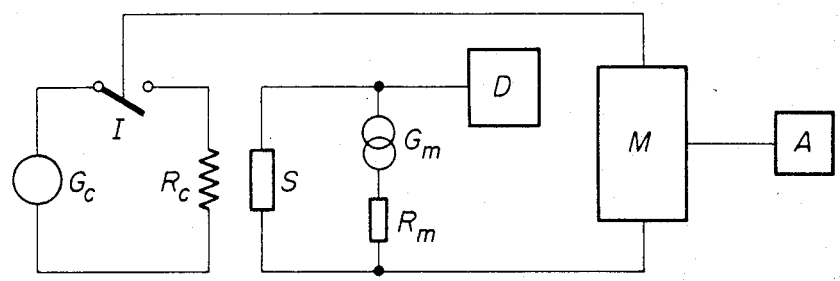
FIG. 3 is a block diagram of another embodiment of this device.

The varying embodiment illustrated in FIG. 3 shows a circuit diagram in which probe S is heated indirectly by a heated resistance $R_c$ supplied by a generator $G_c$ connected to the heating resistance by a switch I controlled by microprocessor M as described for the embodiment shown in FIG. 1. Probe S is supplied, for the measurement, by a current generator $G_m$ through a resistance $R_m$ the value of which is very much higher than that of the probe. Since the heating currents and voltages are galvanically isolated from probe S, the microprocessor M no longer acts on the threshold detector D as in the diagram of FIG. 1.

Figure 4:
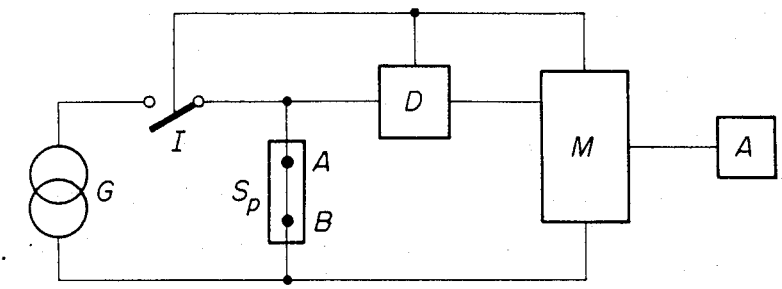
FIG. 4 is a block diagram of yet another embodiment of this device.
Figure 5:
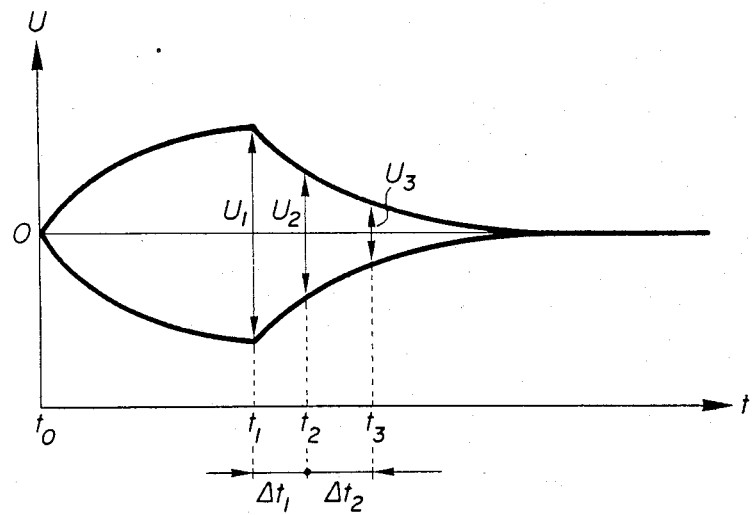
FIG. 5 is a diagram of the variation in voltage recorded on this latter varying embodiment.

FIG. 4 relates to another varying embodiment in which probe $S_p$ consists of a Peltier component the two junctions A and B of which are immersed in the fluid to be measured and which is supplied by a current generator G through a switch I controlled by microprocessor M. As in the example of FIG. 1, microprocessor M is connected to the threshold detector D so as to return the starting point of the measurement curve to the voltage level $U_1$ (FIG. 5) corresponding to the end of cooling voltage of the Peltier component so as to take into account the voltage drop due to the internal resistance of this Peltier component.

The operation of this varying embodiment is as follows: the current generator G supplies the Peltier component $S_p$ and the threshold detector measures the difference in potential at its terminals following the cooling of the cold junction and the heating up of the hot junction A and B. As shown by the diagram, the first threshold $U_1$ is reached which corresponds to a characteristic difference in potential of a first temperature threshold. At that moment, the threshold detector D gives up its information to microprocessor M which opens switch I. The fluid which circulates then tends to return the temperature of junctions A and B to a common value corresponding to the temperature of that fluid and to a nil difference in potential. This reduction in the difference of the temperatures of points A and B gives rise to a variation in voltage which tends towards zero and during this variation in voltage due to the Seebeck effect, measurements are taken of the times $\Delta t_1$ and $\Delta t_2$ which have elapsed between voltage variation $U_1$ and voltage variation $U_2$ and then $U_3$, which variation has been set beforehand by the threshold detector.

The mathematical treatment is the same as that previously outlined. This varying embodiment is interesting, in particular, with regard with the measurement of hot fluids.

I claim:

1. A process for the determination of at least one instantaneous parameter of a fluid linked to the thermal exchange of a probe immersed in said fluid, comprising the steps of raising the temperature of said probe immersed in said fluid to a first given value, setting a second and a third value of the temperature of said probe, measuring the times elapsed as the temperature goes from the first to the second value and from the second value to the third value, and calculating from the resulting measurement at least one parameter linked to the coefficient of thermal exchange and the temperature of the fluid.

2. A process according to claim 1 wherein the same measurement procedures are repeated.

3. An apparatus for determining at least one instantaneous parameter of a fluid which comprises:
 a probe immersed in said fluid;
 means for raising the temperature of said probe to a first given value;
 means for setting a second and a third value of a temperature of said probe;
 means for measuring the times elapsed as the temperature goes from said first value to said second value and from said second value to said third value; and
 means for calculating from the resulting measurements at least one parameter linked to the coefficient of thermal exchange and the temperature of said fluid.

* * * * *